US011612765B2

(12) United States Patent
Fallone et al.

(10) Patent No.: US 11,612,765 B2
(45) Date of Patent: Mar. 28, 2023

(54) REAL-TIME MRI-PET-GUIDED RADIOTHERAPY SYSTEM WITH DOSE-DEPOSITION VERIFICATION

(71) Applicant: ALBERTA HEALTH SERVICES, Edmonton (CA)

(72) Inventors: B. Gino Fallone, Edmonton (CA); Brad Murray, Sherwood Park (CA)

(73) Assignee: ALBERTA HEALTH SERVICES, Edmonton (CA)

( * ) Notice: Subject to any disclaimer, the term of this patent is extended or adjusted under 35 U.S.C. 154(b) by 928 days.

(21) Appl. No.: 16/322,038

(22) PCT Filed: Jul. 31, 2017

(86) PCT No.: PCT/CA2017/050916
§ 371 (c)(1),
(2) Date: Jan. 30, 2019

(87) PCT Pub. No.: WO2018/023195
PCT Pub. Date: Feb. 8, 2018

(65) Prior Publication Data
US 2019/0184197 A1   Jun. 20, 2019

Related U.S. Application Data

(60) Provisional application No. 62/369,146, filed on Jul. 31, 2016.

(51) Int. Cl.
*G01T 1/16* (2006.01)
*A61N 5/10* (2006.01)
(Continued)

(52) U.S. Cl.
CPC ............... *A61N 5/107* (2013.01); *A61N 5/10* (2013.01); *A61N 5/1049* (2013.01);
(Continued)

(58) Field of Classification Search
CPC ........ A61N 5/107; A61N 5/10; A61N 5/1049; A61N 5/1071; A61N 2005/1052;
(Continued)

(56) References Cited

U.S. PATENT DOCUMENTS 7,620,142 B1 * 11/2009 Toth ....................... A61B 6/032
378/108
8,983,573 B2   3/2015 Carline et al.
(Continued)

FOREIGN PATENT DOCUMENTS

CN            104161532 A   * 11/2014   ............. A61B 6/037

OTHER PUBLICATIONS

Translation of CN-104161532-A (Year: 2014).*
(Continued)

*Primary Examiner* — David P Porta
*Assistant Examiner* — Mamadou Faye
(74) *Attorney, Agent, or Firm* — Alston & Bird LLP

(57) ABSTRACT

A radiotherapy system is configured to determine in vivo dose deposition of a radiotherapy treatment beam. The system includes the following components. A bi-planar magnetic resonance imaging (MRI) apparatus comprising a pair of spaced apart magnets. One of the magnets includes a hole proximal the centre thereof. A treatment beam source configured to generate a radiotherapy treatment beam. The treatment beam source is positioned to transmit the treatment beam through the hole in the magnet. A patient support configured to position a patient with the system so that a treatment target is proximal the treatment beam. A Positron Emission Tomography (PET) detector configured to obtain PET data of the treatment beam impacting the patient. The PET detector is positioned so that a transverse section of the patient that includes the treatment target lies between opposing portions of the PET detector.

11 Claims, 6 Drawing Sheets

(51) Int. Cl.
*G01T 1/02* (2006.01)
*G01T 1/166* (2006.01)
*G01T 1/164* (2006.01)

(52) U.S. Cl.
CPC .............. *A61N 5/1071* (2013.01); *G01T 1/02* (2013.01); *G01T 1/1603* (2013.01); *A61N 2005/1052* (2013.01); *A61N 2005/1055* (2013.01); *A61N 2005/1087* (2013.01); *G01T 1/164* (2013.01); *G01T 1/166* (2013.01)

(58) Field of Classification Search
CPC .... A61N 2005/1055; A61N 2005/1087; G01T 1/1603; G01T 1/02; G01T 1/164; G01T 1/166
See application file for complete search history.

(56) References Cited

U.S. PATENT DOCUMENTS

| | | | |
|---|---|---|---|
| 9,468,777 B2 | 10/2016 | Fallone et al. | |
| 9,599,687 B2 * | 3/2017 | Shvartsman | G01R 33/3642 |
| 9,764,162 B1 * | 9/2017 | Willcut | G06T 7/0014 |
| 2008/0039712 A1 * | 2/2008 | Graves | A61B 5/055 |
| | | | 600/411 |
| 2015/0087960 A1 | 3/2015 | Terffert | |
| 2016/0228727 A1 | 8/2016 | Wachowicz et al. | |

OTHER PUBLICATIONS

International Search Report and Written Opinion for Application No. PCT/CA2017/050916, dated Sep. 1, 2017, 9 pages.

Harald Paganetti, Range Uncertainties in Proton Therapy and the Role of Monte Carlo Simulations [article, online], 2013, [retrieved May 1, 2019], retrieved from the Internet <URL: https://www.ncbi.nlm.nih.gov/pmc/articles/PMC3374500/>, 27 pages.

Yang et al., Comprehensive Analysis of Proton Range Uncertainties Related to Patient Stopping-Power-Ratio Estimation Using the Stoichiometric Calibration [article, online], 2012, [retrieved May 1, 2019], retrieved from the Internet <URL: https://www.ncbi.nlm.nih.gov/pubmed/22678123>, 32 pages.

* cited by examiner

REAL-TIME MRI-PET-GUIDED RADIOTHERAPY SYSTEM WITH DOSE-DEPOSITION VERIFICATION

CROSS-REFERENCE TO RELATED APPLICATIONS

This application is a National Stage Application, filed under 35 U.S.C. § 371, of International Application No. PCT/CA2017/050916, filed Jul. 31, 2017, which claims priority to U.S. Provisional Application No. 62/369,146, filed Jul. 31, 2016; the contents of all of which are hereby incorporated by reference in their entireties.

The present invention relates generally a combined Magnetic Resonance Imaging (MRI) and Positron Emission Tomography (PET) radiotherapy systems and particularly to such systems configured to provide dose-deposition verification.

BACKGROUND

External beam radiotherapy involves irradiation of a tumour using a beam created by beam sources such radioactive sources, for example Cobalt, linear accelerators (linacs), or cyclotrons. Beams generated by such sources include photon beams and particle beams, such as protons, carbons, and hadrons, for example. In-vivo direct dose measurement of dose deposition of the beam is very difficult. Typically, the dose deposition is calculated from the geometry of the beam source with respect to the location of the tumour. The ability to measure the deposited dose directly has long been desired, but has not been practical with existing technologies.

Particle therapy is a very precise modality of radiotherapy that involves the use of ions, protons, carbons or heavier ions such as hadrons. The more widely used techniques in RT such as photon beams result in a high dose near the surface which decreases gradually as the beam traverses the subject. Particle therapy, however, has a low uniform dose in the tissue overlying the tumour, then a much higher dose deposition in the tumour due to the "Bragg Peak". Beyond the Bragg Peak there is minimal dose deposited. The depth of the Bragg Peak is determined by the energy of the incident proton beam and the density of the overlying material. The Bragg Peak is very narrow for any given proton energy, so the beam energy must be varied in order to spread the Bragg Peak in order to cover the entire tumour. If the density of the overlying material changes or is not well known, the depth of the Bragg peak may be incorrectly calculated. The fall-off of the Bragg peak is very steep, therefore, uncertainties in the planning of particle therapy treatments would have much more severe consequences than those from photon treatments. Such uncertainties could result in tumours not receiving the required dose, thereby limiting the effectiveness of the treatment. Additionally, surrounding heathy tissues may receive an unwanted dose, resulting in toxicities.

Accordingly, it is an object of the present invention to obviate or mitigate at least some of the above mentioned disadvantages.

SUMMARY

In accordance of an aspect of an embodiment, there is provided a radiotherapy system configured to determine in vivo dose deposition of a radiotherapy treatment beam, the system comprising: a bi-planar magnetic resonance imaging (MRI) apparatus, the bi-planar MRI system comprising a pair of spaced apart magnets, wherein one of the magnets includes a hole proximal the centre thereof; a treatment beam source configured to generate a radiotherapy treatment beam, the treatment beam source positioned to transmit the treatment beam through the hole in the magnet; a patient support configured to position a patient with the system so that a treatment target is proximal the treatment beam; and a Positron Emission Tomography (PET) detector configured to obtain PET data of the treatment beam impacting the patient, the PET detector positioned so that a transverse section of the patient that includes the treatment target lies between opposing portions of the PET detector.

In an embodiment, the PET detector comprises two opposing arcuate sections, each arcuate section including banks of radiation detectors. For example, the PET detector may be generally tubular in shape and comprise an opening proximal the hole in the magnet The opening is sized and shaped to allow the treatment beam to pass there through. As another example, the arcuate sections may be spaced apart from each other to provide a gap above and below the patient support. As yet another example, the arcuate sections may be spaced apart from each other to provide a gap proximal the hole in the magnet and connected at an end distal from the hole in the magnet.

Depending on the implementation, the PET detector obtains imaging information shortly after generation of the treatment beam or simultaneously with generation of the treatment beam.

The PET data comprises one or both of Bragg peak depth information and imaging information.

In accordance with another aspect of an embodiment, there is provided a method for dynamically improving in vivo dose deposition of a radiotherapy treatment beam, the method comprising: positioning a patient at a predetermined treatment position; applying the treatment beam based on a treatment plan determined in a pre-treatment phase; receiving imaging information from a Magnetic Resonance Imagining (MRI) apparatus, the imaging information including soft tissue information; receiving Positron Emission Tomography (PET) data from a PET detector, the PET data representing the dose deposition of the treatment beam; and modifying parameters of the treatment beam and/or positioning of the patient to improve the dose deposition based on the received MRI imaging information and the PET data for subsequent application of the treatment beam.

In an embodiment, the method further determines a difference in the dose deposition based on the received PET data and a target dose deposition defined in the treatment plan The parameters of the treatment beam and/or the position of the patient are modified to reduce the difference.

In an embodiment, the dose deposition information is determined at the PET detector in response to photons being generated from an interaction of the treatment beam with the patient. For example, the photons are generated in response to particles generated by the treatment beam impacting the patient interacting with complementary particles in the patient. As another example, the photons are generated in response to particles generated by a tracer injected in the patient interacting with complementary particles in the patient. The tracer is configured to concentrate in tissue affected by the treatment beam.

When using the tracer, the method further comprises: obtaining pre-treatment PET data from the PET detector during the pre-treatment stage; determining a difference between the PET data and the pre-treatment PET data; and using the difference to modify the parameters of the treatment beam and/or the positioning of the patient to improve the dose deposition.

BRIEF DESCRIPTION OF THE DRAWINGS

Embodiment of the present invention will now be described by way of example only, with reference to the following drawings in which.

DETAILS DESCRIPTION OF THE PREFERRED EMBODIMENTS

Figure 1A:
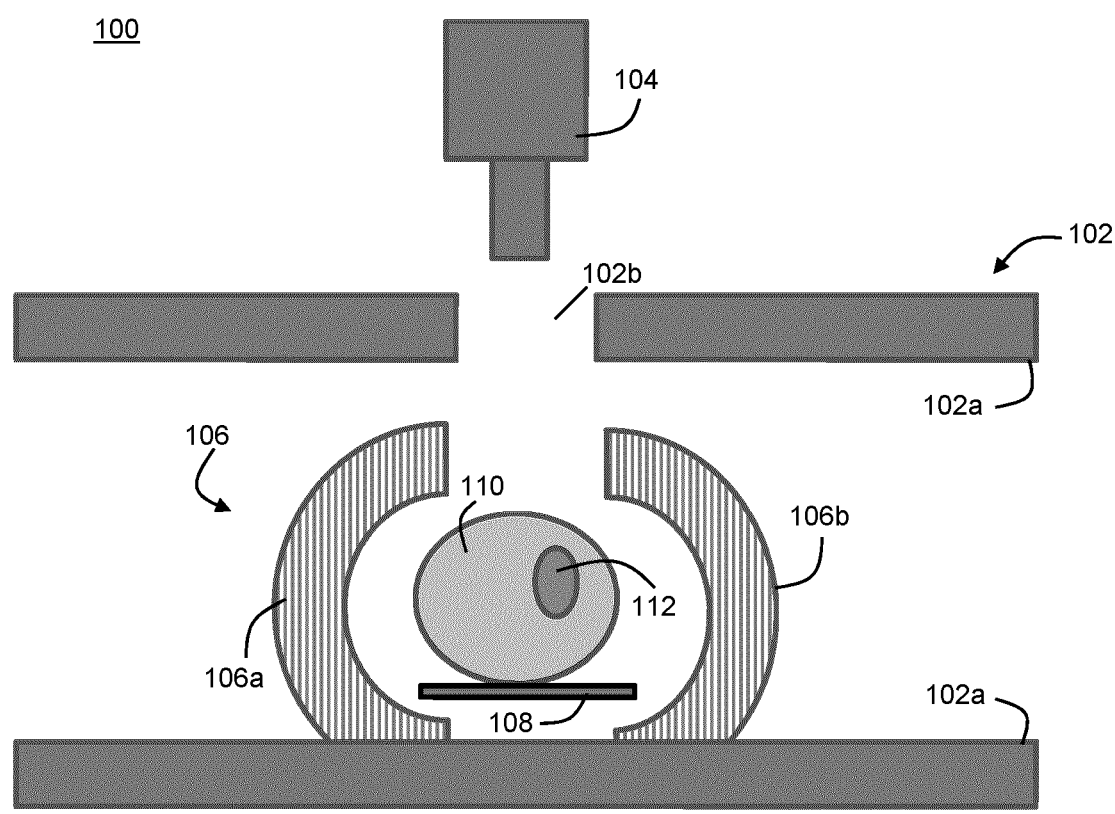
FIGS. 1a and 1b illustrate a radiotherapy system in accordance with an embodiment.
Figure 1B:
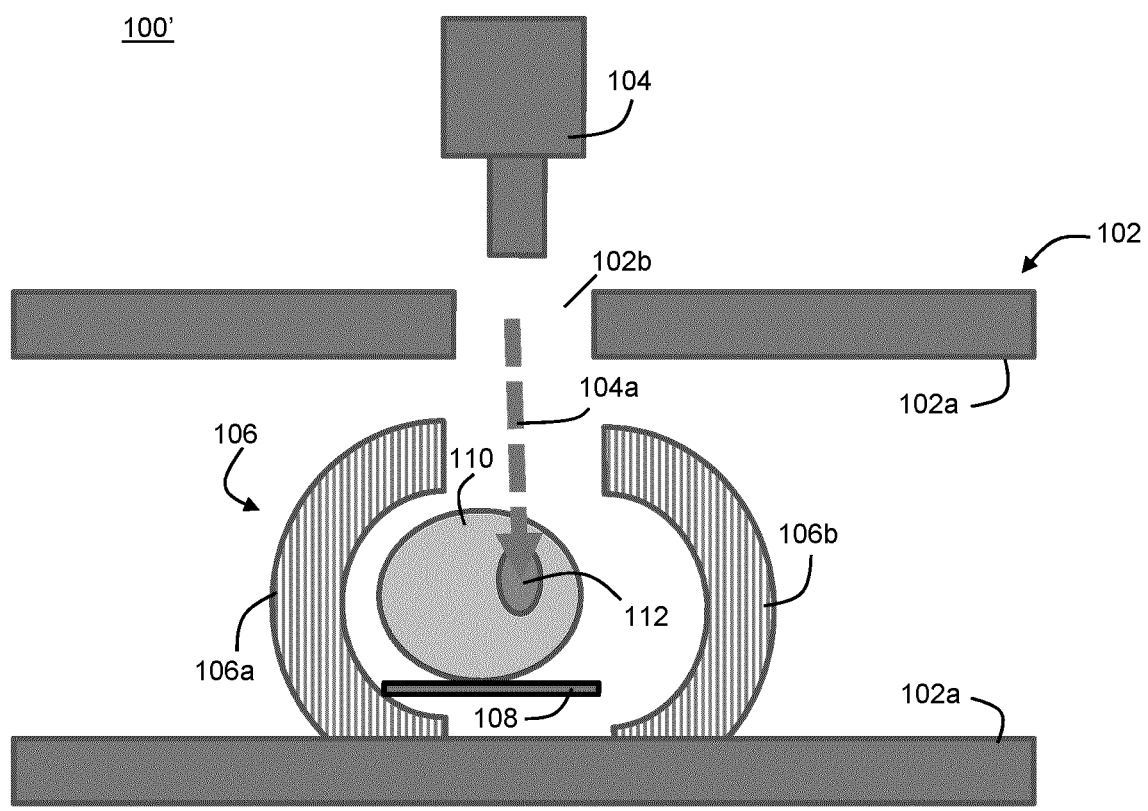

For convenience, like numerals in the description refer to like structures in the drawings. Referring to FIGS. 1a and 1b, a combined MRI-PET radiotherapy system in accordance with an embodiment of the present invention is illustrated generally by numeral 100. The radiotherapy system 100 includes a bi-planar MRI apparatus 102, a treatment beam source 104, and a PET detector 106. A patient support 108, such as a patient couch, is positioned within the radiotherapy system 100.

The bi-planar MRI apparatus 102 comprises a pair of spaced apart planar magnets 102a. A hole 102b is provided proximal the centre of one of the magnets 102a. The treatment beam source 104 is configured to generate a radiotherapy treatment beam 104a. The treatment beam 104a may comprise photons or particles, such as protons, carbons, hadrons, and the like. The treatment beam source 104 is positioned so that the treatment beam 104a passes through the hole 102b in the magnet 102a. In an embodiment, the MRI apparatus 102 and the beam source 104 are coupled to a common gantry (not shown) so that they may be rotated in unison. The combination of the MRI apparatus 102 and treatment beam source 104 is described in detail in U.S. Pat. No. 9,468,777 to Fallone et al., titled "Integrated External Beam Radiotherapy and MRI System" and U.S. Pat. No. 8,983,573 to Carlone et al., titled "Radiation Therapy System".

The patient support 108 is initially positioned at a set-up position, which is at the geometric centre of the radiotherapy system 100, as shown in FIG. 1a. A patient 110 is placed onto the patient support 108 in the set-up position. Once the patient 110 has been placed onto the patient support 108, the patient support 108 can be moved laterally and/or vertically as necessary to a treatment position. In the treatment position, a treatment target 112, such as a tumour, is positioned at the geometric centre of the radiotherapy system 100, as shown in FIG. 1b. This places the tumour 112 proximate the isocentre of the treatment beam 104a during treatment. The patient support 108 can be transitioned back to the set-up position to facilitate rotation of the radiotherapy system 100 and removal of the patient 110 from the radiotherapy system 100. Translation of the patient support 108 is described in detail in U.S. Patent Application Publication No. 2016/0228727 by Wachowicz et al., titled "Peripheral Tumour Treatment".

The use of the MRI apparatus 102 and treatment beam source 104 combination has been selected because the location of the treatment target may change from a pre-treatment position stage. For example, the variation in the target location may result from positioning issues, organ motion, changes of anatomical structure and the like. Accordingly, real-time guidance provided by such a combination would identify the position of the tumour prior to particle therapy, in addition to any change in the position due to patient motion or patient breathing. At present, MRI is the preferred identifier for a tumour because MRI identifies soft-tissue best and all cancer tumours reside in soft tissue. Furthermore, MRI can provide soft-tissue imaging while irradiating. MRI-guided particle systems can help guide the initial delivery of the particle beam to the location of the tumour in real time. Thus, while irradiating, such systems can avoid uncertainties due to setup and positioning errors, organ motion, and change of anatomical structures, such as the shrinkage of tumors or patient weight-change.

However, although the MRI can be used to accurately determine a position of the treatment target, it can be difficult to determine the dose deposition of the treatment beam 104a due to particle range uncertainties. Specifically, there are several sources of error in calculating the particle range that cannot be resolved with MRI alone. Particle-range uncertainties can be caused by stochastic errors, uncertainties in the Hounsfield unit (HU) conversion method, and the uncertainties of directly converting MRI data to electron densities and stopping powers. The HU conversion method is described by Paganetti in "Range uncertainties in proton therapy and the role of Monte Carlo simulations", Phys Med Biol. 2012; 57: R99-117 doi:10.1088/0031-9155/57/11/R99 and by Yang M, Zhu X R, Park P C, Titt U, Mohan R, Virshup G, et al. in "Comprehensive analysis of proton range uncertainties related to patient stopping-power-ratio estimation using the stoichiometric calibration", Phys Med Biol. 2012; 57: 4095-115 doi:10.1088/0031-9155/57/13/4095.

Conversion of empirically derived HU from Computed Tomography (CT) and MRI to relative stopping powers used in pre-treatment stage planning calculations cannot be directly validated in vivo. This causes range uncertainties in the calculations which may result in under-treating tumours and over-treating healthy tissue. In addition, multiple Coulomb scattering and non-elastic nuclear reactions, especially at interfaces of alternating low- and high-density tissues interfaces cannot be adequately modeled from electron density distribution currently best provided by CT.

In vivo monitoring of dose deposition can currently be done in photon therapy with projection imaging of the photon beam. However, this technique is virtually impossible in proton therapy because the proton therapy beam does not completely exit the body for imaging. Accordingly, use of implanted monitors would be required, which is invasive and difficult. Although MRI can be used to measure the physiological changes in proton irradiated tissues, such as the fatty replacement of vertebra bone marrow, this cannot be used for real time dose depositions validation, since the physiological changes take several weeks to develop. PET-based detection of proton induced positron emitters is an approach that is being used in a practical manner. PET-based detection can be used to determine the proton range, such as through prompt gamma detection, or by performing imaging. Although, it is not presently possible to perform PET imaging in real-time, it may be possible to do so as technology advances. Accordingly, the following embodiments are discussed with reference to gamma detection to determine the proton range, or Bragg peak depth. However, imaging may also be performed if it is technologically feasible to do so.

Some PET-MRI systems are commercially available for diagnostic imaging purposes. In these systems, PET-emitting isotopes attached to pharmaceuticals are injected into a patient resulting in PET image to visualize the in vivo distribution of the radiopharmaceutical. At the same time, MRI is performed on the patient to provide visualization of the soft-tissue anatomy. Current PET-MRI system involve a cylindrical MRI surrounding a ring of PET detectors. This configuration is impractical, if not impossible for on-line guidance and verification of proton therapy. For such systems, the proton therapy beam must enter through the edge of the cylindrical magnet and the PET detectors. Such a geometry would cause significant interaction between the cylindrical magnet, the PET detectors, and the proton beam, Such interaction results in the production of significant radiation making imaging difficult, if not impossible. Furthermore, the MRI main magnetic field, $B_o$ would be transverse to the central axis of the particle beam resulting in significant deflection.

Accordingly, in an embodiment, the PET detector 106 is positioned between the magnets 102a of the MRI apparatus 102. The PET detector 106 comprises two opposing arcuate sections 106a and 106b. Each arcuate section 106a and 106b of the of the PET detector 106 includes banks of radiation detectors that allow the radiotherapy system 100 to detect coincidence of two particles that reach the opposed detectors at the same time. The arcuate sections 106a and 106b are spaced apart from each other to provide a gap above and below the patient support 108. Such a gap allows the treatment beam 104a to treat the patient 110 unimpeded.

The arcuate sections 106a and 106b of the PET detector 106 are positioned so that a transverse section of the patient 110 that includes the treatment target 112 lies between the arcuate sections 106a and 106b of the PET detector 106 when the patient 110 is in the treatment position. Accordingly, the length of each arcuate section 106a and 106b is sufficient to encompass a region of the patient 110 that includes the treatment target 112. In an embodiment, the length of the PET detector is between 16 cm and 22 cm, although the length may vary depending on the implementation.

In one embodiment, the treatment beam 104a interacts with the patient 110 to generates photons detectable by the PET detector 106. For example, when the treatment beam 104a is a proton beam, positrons are produced from interactions of the proton beam with the patient 110. These positrons collide with electrons within the patient 110 to create annihilation photons. The PET detector 106 has sufficient energy discrimination to distinguish photons that are 511 KeV, which is the photon energy of the created annihilation photons. Thus, the radiotherapy system 100 will be able to detect the annihilation photons that are emitted following the interaction of the treatment beam 104a with the patient 110. The PET detector 106 can use the detected annihilation photons to provide Bragg peak depth information to determine the dose deposition of the treatment beam 104a in real-time.

In another embodiment, the interaction of treatment beam 104a with the patient 110 does not, on its own, generate photons detectable by the PET detector 106. For example, photon beams generated by linacs or cobalt systems do not generate positrons when they interact with the patient 110. In such an embodiment, the PET detector 106 can be configured to detect photons produced as a result of a tracer that is injected in the patient 110 prior to treatment. For example, a PET radiotracer such as fluorodeoxyglucose (FDG) can be used. FDG emits positrons created through β+ decay. Similar to the previous embodiment, the positrons created through β+ decay collide with electrons within the patient 110 to create annihilation photons. Further, large radiation doses can cause a significant amount of trauma, or inflammation. Thus, areas of the patient 110 affected by the treatment beam 104a will demonstrate the trauma. Accordingly, specific biological molecules can be designed to concentrate in tissue that has been traumatized. The biological molecules can then be tagged with the radiotracer and injected into the patient 110. The PET detector 106 can detect positrons emitted by the radiotracer to obtain Bragg peak depth information about the traumatized tissue and, therefore, the dose deposition of the treatment beam 104a, in near real-time.

Specifically, the radiotracers will continue to emit positrons through β+ decay even after the treatment beam 104a is inactive. Accordingly, it is possible to improve determination of the dose deposition by rotating the gantry such that Bragg peak depth information is gathered from many imaging angles, thus capturing PET detector 106 data from the full 360 degrees around the patient 110.

Once the in vivo dose deposition of the treatment beam 104a is known, the parameters of the treatment beam 104a can be adjusted iteratively to maximize treatment of the treatment target 112 and minimize damage to surrounding tissue.

Although the radiotherapy system is described with respect to a particular configuration of the PET detector 106, other configurations of the PET detector 106 may also be used. For example, in an alternative embodiment, the two arcuate sections 106a and 106b of the PET detector 106 may be connected at an end distal from the hole 102b in the magnet 102a. In yet an alternative embodiment, the PET detector 106 may be generally tubular in shape with an opening positioned proximal the hole 102b in the magnet 102a. Such an opening would be sized sufficiently large for the treatment beam 104a to pass through unimpeded.

Figure 1C:
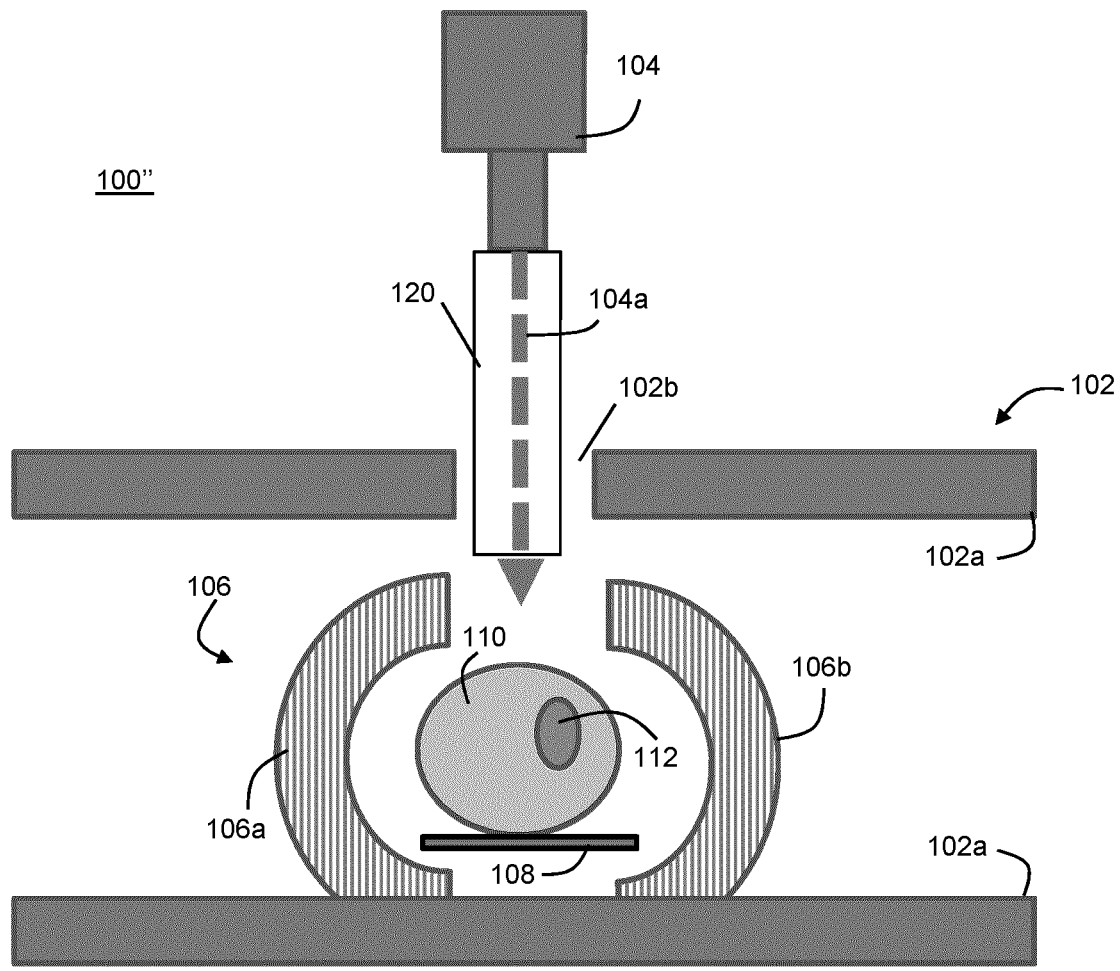
FIG. 1c illustrates the radiotherapy system of claims 1a and 1b further including a vacuum column.

Referring to FIG. 1c, in yet an alternate embodiment, the radiotherapy system 100" further includes a vacuum column 120. The vacuum column 120 extends from the end of the treatment beam source 104, through the hole 102b in the magnet 102a to a position proximal the patient 110. The treatment beam 104a passes from the treatment beam source 104 through the vacuum column 120 and exits proximal the patient 110. Such a configuration allows calculations for the treatment beam 104a to be determined as if the treatment beam 104a was exiting the treatment beam source 104, directly, proximal the patient 110.

Figure 2:
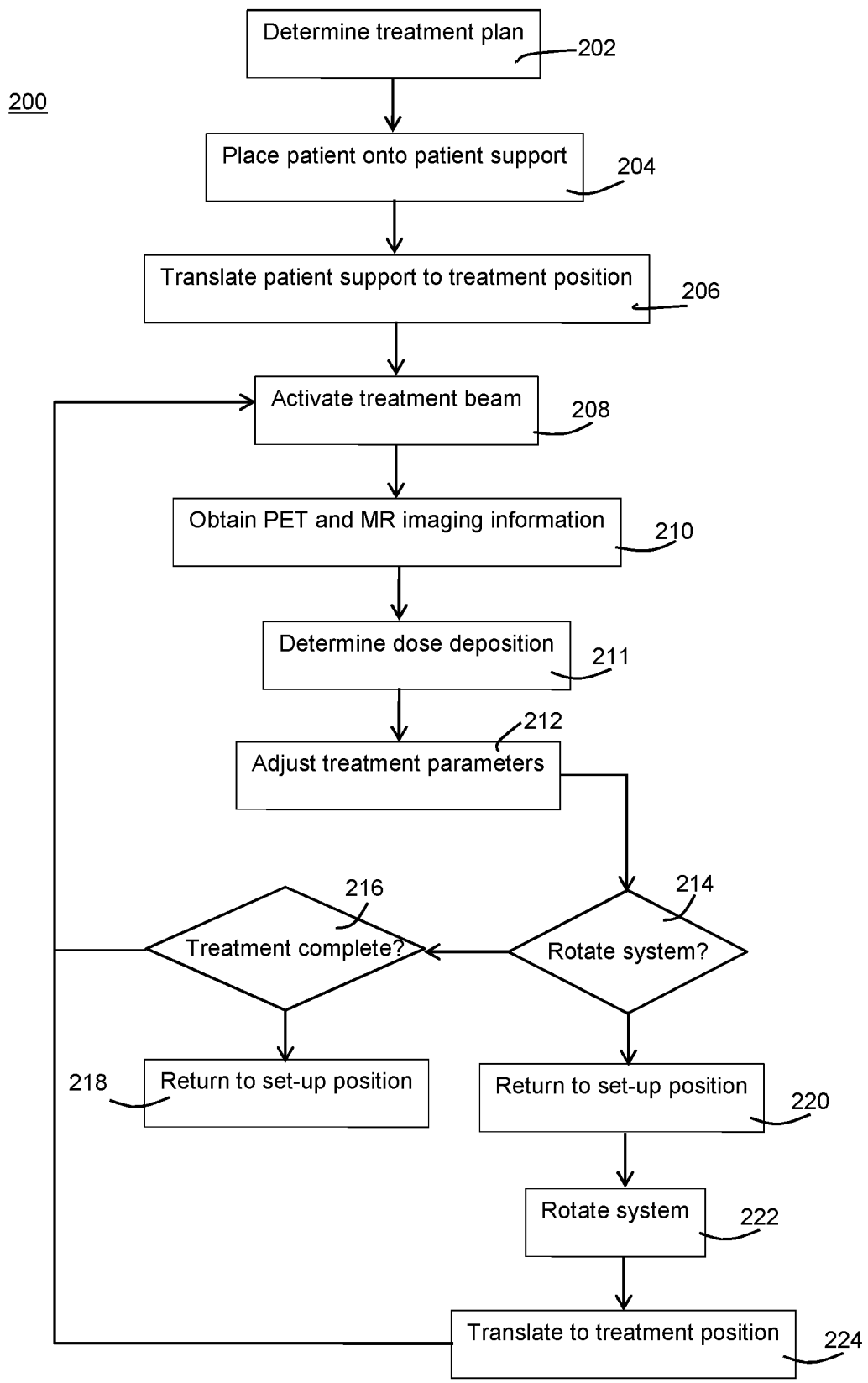
FIG. 2 is flowchart illustrating the operation of the radiotherapy system when a treatment beam generates particles detectable by a PET detector.

Referring to FIG. 2, a flow chart illustrating operation of the radiotherapy system 100 is illustrated generally by numeral 200. The method illustrated in FIG. 2 is for a treatment beam 104a that generates photons detectable by the PET detector 106 as a result of the interaction between the treatment beam 104a and the patient 110. For example, when the treatment beam is a proton beam, as discussed above, annihilation photons are generated upon interaction with the patient 110.

At step 202, in a pre-treatment phase, an MR image of the patient 110 is obtained and a treatment plan is determined. At step 204, the patient 110 is placed onto the patient support 108. At step 206, the patient support 108 is translated to the treatment position.

At step 208 the treatment beam 104a is activated. Simultaneously, at step 210, the PET detector 206 determines Bragg peak depth information based on reception of the annihilation photons, thereby providing an indication of the dose deposition of the treatment beam 104a. Additionally, the MRI apparatus 104 obtains MR imaging information of the soft tissue of the patient 110.

At step 211, the Bragg peak depth information is analysed in conjunction with the MR image information and compared with a treatment plan to determine whether or not the treatment target 112 is receiving maximal treatment and the surrounding tissue is being minimally affected. At step 212, parameters of the treatment beam 104a and/or the location of the treatment position are modified to direct the dose deposition of the treatment beam 104a to the treatment target 112. The analysis and parameter modification may be performed by a clinical expert or computer software.

At step 214, it is determined if the radiotherapy system 100 is to be rotated to treat the treatment target 112 from a different angle. If not, then at step 216, it is determined whether or not the treatment plan is complete. If the treatment plan is complete, then at step 218 the patient support 108 is returned to the set-up position and the patient 110 is removed from the radiotherapy system 100. If the treatment plan is not complete, then the method returns to step 208.

Returning to step 214, if the radiotherapy system 100 is to be rotated, then at step 220, the patient support 108 is returned to the set-up position. At step 222, the radiotherapy system 100 is rotated to the next treatment angle and at step 224 the patient support 108 is translated to the treatment position. The method then returns to step 208.

Figure 3A:
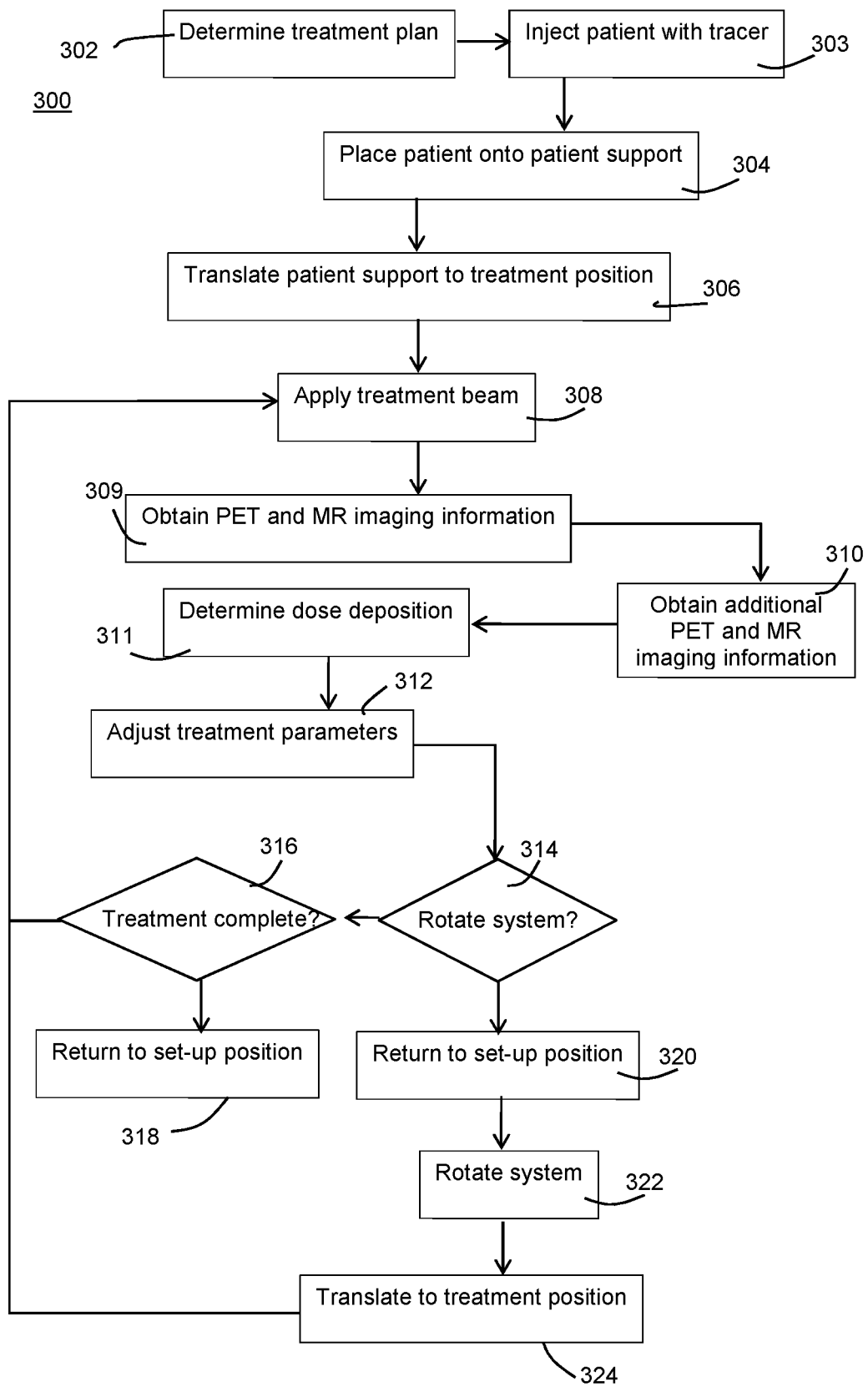
FIGS. 3a and 3b are flowcharts illustrating the operation of the radiotherapy system when an injectable tracer generates particles detectable by a PET detector.
Figure 3B:
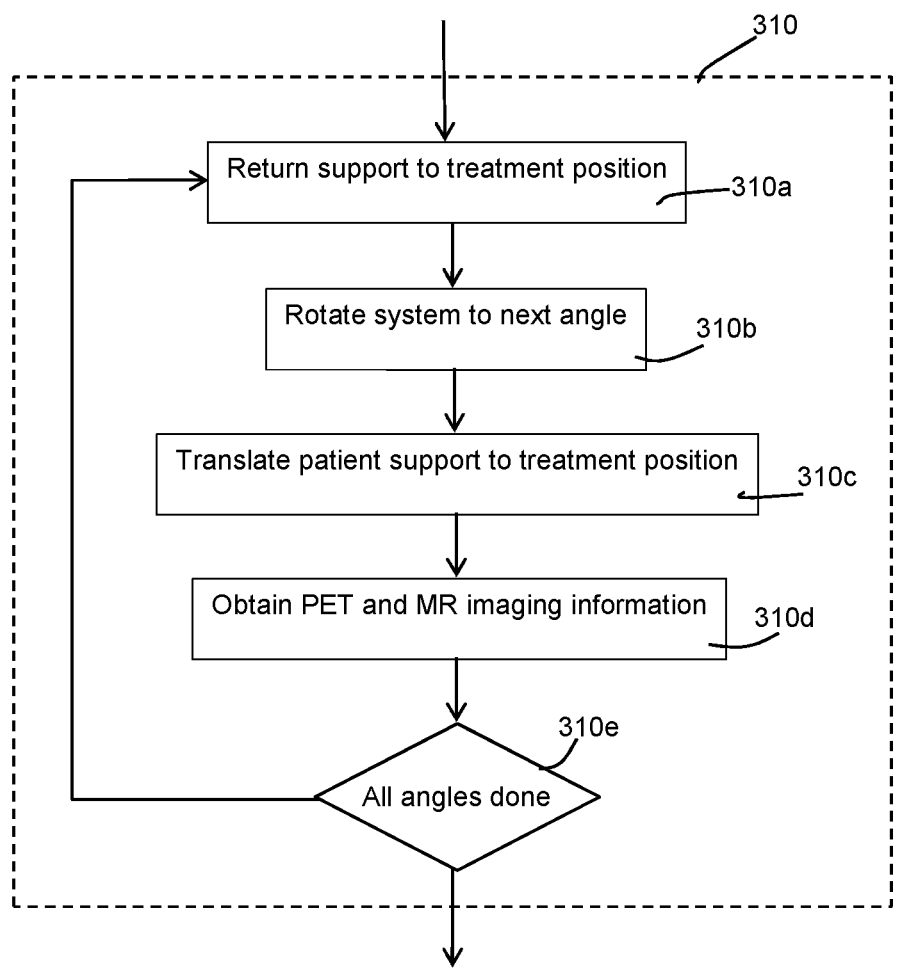

Referring to FIGS. 3a and 3b, a flow chart illustrating operation of the radiotherapy system 100 is illustrated generally by numeral 200. The method illustrated in FIG. 3 is for a treatment beam 104a that does not, on its own, generate photons detectable by the PET detector 106. For example, the photon beams generated by linacs or cobalt systems, as previously discussed, require a PET radiotracer to be injected into the patient 110. As discussed, the PET radiotracer generates positrons that interact with electrons within the patient 110 to create annihilation photons.

At step 302, in a pre-treatment phase, a treatment plan is determined. In order to facilitate determination of the treatment plan, an MR image of the patient 110 is obtained. Additionally, the radioactive tracer is injected into the patient 110 and reference PET Bragg peak depth information is determined. The pre-treatment phase may occur well in advance of the treatment, but is better if it is done shortly before the treatment. Accordingly, at step 303, the patient 110 is injected with the radioactive tracer. At step 304, the patient 110 is placed onto the patient support 108. At step 306, the patient support 108 is translated to the treatment position.

At step 308 the treatment beam 104a is applied to the patient 110. At step 309 the PET detector 206 determines Bragg peak depth information based on reception of the annihilation photons, thereby providing an indication of the dose deposition of the treatment beam 104a. Additionally, the MRI apparatus 104 obtains MR imaging information of the soft tissue of the patient 110.

At step 310, the Bragg peak depth information is acquired a number of times, from different angles, by rotating the radiotherapy system 100. Specifically, at step 310a, the patient support 108 is returned to the set-up position. At step 310b, the radiotherapy system 100 is rotated to the next imaging angle. At step 310c, the patient support 108 is translated to the treatment position. At step 310d, additional Bragg peak depth information is acquired. At step 310e it is determined if Bragg peak depth information has been acquired from all desired imaging angles. If not, then the method returns to step 310a. Otherwise, the method returns to step 311.

At step 311, the PET Bragg peak depth information is analysed in conjunction with the MR image information and compared with a treatment plan to determine whether or not the treatment target 112 has received maximal treatment and the surround tissue has been minimally affected. Part of this analysis includes calculating a difference between the PET Bragg peak depth information obtained after application of the treatment beam 104a and the PET Bragg peak depth information obtained during the pre-treatment phase. This difference it used to determine the trauma likely caused by the application of the treatment beam 104a. At step 312, parameters of the treatment beam 104a and/or the location of the treatment position are modified to direct the dose deposition of the treatment beam to the treatment target 112. The analysis and parameter modification may be performed by a clinical expert or computer software.

At step 314, it is determined if the radiotherapy system 100 is to be rotated to treat the treatment target 112 from a different angle. If not, then at step 316, it is determined whether or not the treatment plan is complete. If the treatment plan is complete, then at step 318 the patient support 108 is returned to the set-up position and the patient 110 is removed from the radiotherapy system 100. If the treatment plan is not complete, then the method returns to step 308.

Returning to step 314, if the radiotherapy system 100 is to be rotated, then at step 320, the patient support 108 is returned to the set-up position. At step 322, the radiotherapy system 100 is rotated to the next treatment angle and at step 324 the patient support 108 is translated to the treatment position. The method then returns to step 308.

Although preferred embodiments of the invention have been described herein, it will be understood by those skilled in the art that variations may be made thereto without departing from the scope of the appended claims.

What is claimed is:

1. A radiotherapy system configured to determine dose deposition of a radiotherapy treatment beam in a patient, the system comprising:
   a bi-planar magnetic resonance imaging (MRI) apparatus, the bi-planar MM system comprising a pair of spaced apart planar magnets, wherein one of the magnets includes a hole proximal the centre thereof;
   a treatment beam source configured to generate a radiotherapy treatment beam, the treatment beam source positioned to transmit the treatment beam through the hole in the magnet;
   a patient support configured to position the patient with the system so that a treatment target is proximal the treatment beam; and
   a Positron Emission Tomography (PET) detector configured to obtain PET data of the treatment beam impacting the patient, the PET detector positioned so that a transverse section of the patient that includes the treatment target lies between opposing portions of the PET detector.

2. The system of claim 1, wherein the MRI apparatus, the treatment beam source, and the PET detector are mechanically coupled to a common gantry to facilitation rotation thereof in unison.

3. The system of claim 2, wherein the patient support is configured to move the patient from a set-up position to a treatment position.

4. The system of claim 3, where the patient support is placed in the set-up position to facilitate entry and exit of the patient to the system and rotation of the MRI apparatus, the treatment beam source, and the PET detector.

5. The system of claim 1, wherein the PET detector comprises two opposing arcuate sections, each arcuate section including banks of radiation detectors.

6. The system of claim 5, wherein the PET detector is generally tubular in shape and comprises an opening proximal the hole in the magnet, the opening sized and shaped to allow the treatment beam to pass there through.

7. The system of claim 5, wherein the arcuate sections are spaced apart from each other to provide a gap above and below the patient support.

8. The system of claim 5, wherein the arcuate sections are spaced apart from each other to provide a gap proximal the hole in the magnet and connected at an end distal from the hole in the magnet.

9. The system of claim 1, wherein the PET detector obtains imaging information shortly after generation of the treatment beam.

10. The system of claim 1, wherein the PET detector obtains imaging information simultaneously with generation of the treatment beam.

11. The system of claim 1, wherein the PET data comprises one or both of Bragg peak depth information and imaging information.

* * * * *

UNITED STATES PATENT AND TRADEMARK OFFICE
CERTIFICATE OF CORRECTION

PATENT NO. : 11,612,765 B2
APPLICATION NO. : 16/322038
DATED : March 28, 2023
INVENTOR(S) : B. Gino Fallone et al.

It is certified that error appears in the above-identified patent and that said Letters Patent is hereby corrected as shown below:

In the Claims

In Column 8, Line 43, Claim 1, delete "MM" and insert -- MRI --, therefor.

In Column 8, Line 66, Claim 4, delete "where" and insert -- wherein --, therefor.

Signed and Sealed this
Thirty-first Day of October, 2023

*Katherine Kelly Vidal*

Katherine Kelly Vidal
*Director of the United States Patent and Trademark Office*